US00PP13019P2

(12) United States Plant Patent
Pieters

(10) Patent No.: US PP13,019 P2
(45) Date of Patent: Oct. 1, 2002

(54) CHRYSANTHEMUM PLANT NAMED 'ORANGE URANO'

(76) Inventor: Dirk Pieters, Schierveldestraat 3A, Oosnieuwkerke, 8840 Staden (BE)

( * ) Notice: Subject to any disclaimer, the term of this patent is extended or adjusted under 35 U.S.C. 154(b) by 0 days.

(21) Appl. No.: 09/550,150

(22) Filed: Apr. 17, 2000

(51) Int. Cl.[7] ..... A01H 5/00

(52) U.S. Cl. ..... Plt./290

(58) Field of Search ..... Plt./290

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of chrysanthemum producing flowers with orange ray florets.

1 Drawing Sheet

BACKGROUND OF THE INVENTION

The present invention is directed to a new and distinct variety of *Chrysanthemum morifolium*. The varietal denomination of the new chrysanthemum is 'ORANGE URANO'.

The new variety was discovered as a single branch mutation of 'Red Urano'. The new variety has been asexually reproduced by vegetative cuttings in Ventura County, Calif. and the distinguishing characteristics are retained through successive generations of asexual reproduction.

SUMMARY OF THE INVENTION

'ORANGE URANO' is a chrysanthemum plant that produces flowers with orange ray florets.

COMPARISION WITH PARENTS

'ORANGE URANO' differs from its parent in having different color florets.

BRIEF DESCRIPTION OF ILLUSTRATIONS

The accompanying photograph shows a typical specimen of the plant and flowers of the new variety with colors being as nearly true as possible with illustrations of this type.

DESCRIPTION OF THE PLANT

The following description of the new variety is of specimens grown in a greenhouse in Ventura County, Calif. Plants described are approximately 95 days old from a rooted cutting. 'ORANGE URANO' has not been observed under all possible environmental conditions. The phenotype may vary with variations in the environment such as temperature, light intensity, day length and cultural conditions. The color designations herein are from The *Royal Horticultural Society Colour Chart* except where general terms are used.

To produce a commercial product the plants may be pinched once about ten days after planting. No growth retardant has been applied in the specimens described. Useful growing conditions include average night temperatures of about 17° C. to 20° C. and average day temperatures of about 20° C. to 30° C. No susceptibility or resistance to disease has been observed. Resistance or susceptibility to insects has not been observed. Seed production has not been observed. Winter hardiness and drought/heat tolerance have not been observed.

PLANT

Plant type: Herbaceous perennial.
Growth habit: Mounding.
Size: Height about 25 cm, width about 27 cm.
Growth rate: Moderate.
Branching characteristics: Very free branching, lateral branches are approximately 21 cm.

FOLIAGE

Arrangement: Alternate.
Compound or simple: Simple.
Quantity of leaves: Many.
Leaf size:
- *Length.*—About 6 cm.
- *Width.*—About 3.5 cm.

Leaf shape: Ovate, margin palmately lobed.
Leaf tip: Acuminate.
Leaf base: Attenuate.
Leaf attachment: Stalked.
Petiole: Length about 2 cm, diameter about 0.3 cm. color near 138C.
Margin type: Serrate.
Texture: Lightly pubescent.
Color:
- *Young foliage upper side.*—Near 138A.
- *Young foliage under side.*—Near 138B.
- *Mature foliage upper side.*—Near 138A.
- *Mature foliage under side.*—Near 138A.

Venation: Net.
- *Color.*—Venation upper side: Near 138C. Venation under side: Near 138C.

BLOOM

Inflorescence:
- *Flowering habit.*—Induced by darkness period greater than 13.5 hours. Approximately 50 days of day length required to induce and develop blooms.
- *Inflorescence form.*—Decorative, opening to a multiplex daisy, multiplex daisy is a term used to describe many rows of ray florets and a very small disc presence, when the inflorescence ages the disc florets become visible and create a very small disc, for the majority of the inflorescence life the disc is not visible and the form is considered decorative.

*Natural flowering season.*—Around the last week in August and early September in Ventura County, Calif.
*Quantity of inflorescences per stem.*—About 14.
*Inflorescence diameter.*—About 5.5 cm.
*Inflorescence depth.*—About 2 cm.
*Disc diameter.*—About 1 cm.
*Inflorescence longevity on plant.*—About 20 to 25 days.
*Persistence.*—Persistent.

Ray florets:
*Appearance.*—Matte.
*Texture.*—Smooth.
*Number.*—About 200.
*Shape.*—Oblanceolate.
*Margin.*—Entire.
*Tip.*—Obtuse.
*Length.*—About 4 cm.
*Width.*—About 1.5 cm.
*Color.*—The term "mixed" is used below to imply the coloration of the ray floret is an irregular combination of the described colors. Upper side: First opening: Near 28A mixed with 15A. Mature: Near 32A mixed with 34A. Fading: Near 32A mixed with 28A. Under side: First opening: Near 28B mixed with 16A. Mature: Near 28A. Fading: Near 28A mixed with 17B.

Disc florets:
*Appearance.*—Shiny.
*Texture.*—Smooth.
*Number.*—About 50.
*Shape.*—Cylindric.
*Tip.*—Obtuse.
*Length.*—About 1 cm.
*Width.*—About 0.1 cm.
*Color.*—First opening: Near 17A. Mature: Near 17B. Fading: Near 22A.

Peduncle: About 0.3 cm in diameter.
*Length.*—Terminal, shortest: About 6 cm. Lateral, longest: About 9 cm.
*Color.*—Near 138A.
*Strength.*—Moderate.
*Habit.*—Erect.

Inflorescence bud:
*Length.*—About 1 cm.
*Diameter.*—About 1 cm.
*Form or shape.*—Globular.
*Color.*—Near 32A.

Involucral bracts: Length about 0.8 cm, width about 0.7 cm.
*Appearance.*—Matte.
*Texture.*—Lightly pubescent.
*Number.*—About 20 to 30.
*Shape.*—Ovate.
*Margin.*—Entire.
*Tip.*—Acute.
*Color.*—Upper side: Near 138A. Under side: Near 138A.

REPRODUCTIVE ORGANS

Ray florets:
*Pistillate.*—Pistil length in the ray florets is about 1.1 cm. Pistil number: 1 per flower. Stigma shape: 2 branched. Stigma color: Near 7A. Style length: About 1 cm. Style color: Near 6D.

Disc florets:
*Pistillate.*—Pistil length in the disc florest is about 1 cm. Pistil number: 1 per flower.
*Stigma shape.*—Cylindric.
*Style length.*—About 0.8 cm.

Staminate:
*Stamen number.*—About 5.
*Anther shape.*—Tubular.
*Anther color.*—Near 16A.
*Pollen color.*—Near 23B.

What is claimed:

1. A new and distinct chrysanthemum plant of the variety substantially as herein shown and described.

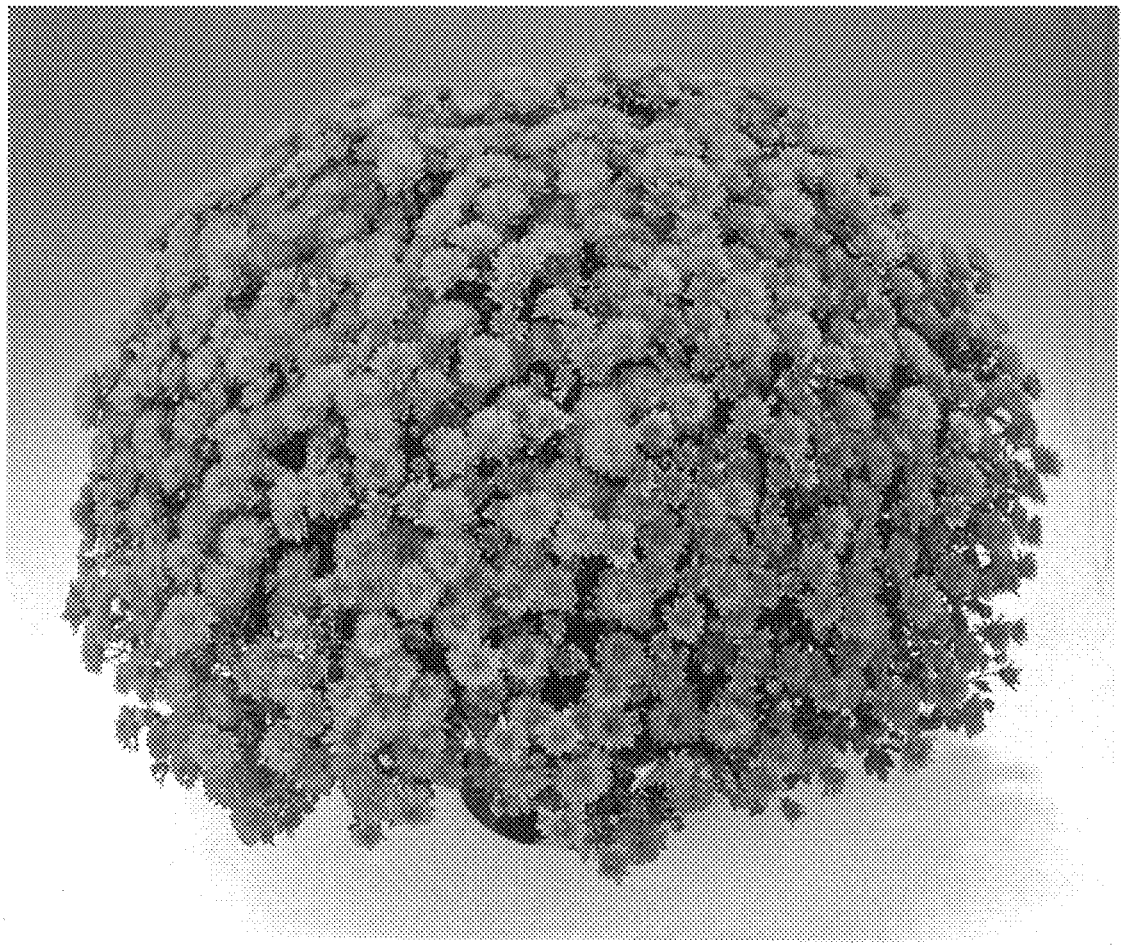

* * * * *